United States Patent
Katrana et al.

(10) Patent No.: US 9,084,680 B2
(45) Date of Patent: Jul. 21, 2015

(54) MULTIPLE BEARING HUMERAL PROSTHESIS

(71) Applicant: Biomet Manufacturing, LLC, Warsaw, IN (US)

(72) Inventors: Nicholas J. Katrana, Fort Wayne, IN (US); Nathan A. Winslow, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 0 days.

(21) Appl. No.: 13/632,199

(22) Filed: Oct. 1, 2012

(65) Prior Publication Data

US 2013/0090736 A1 Apr. 11, 2013

Related U.S. Application Data

(60) Provisional application No. 61/543,477, filed on Oct. 5, 2011.

(51) Int. Cl.
*A61F 2/40* (2006.01)
*A61F 2/30* (2006.01)

(52) U.S. Cl.
CPC ............. *A61F 2/4014* (2013.01); *A61F 2/4059* (2013.01); *A61F 2/4081* (2013.01); *A61F 2002/30332* (2013.01); *A61F 2002/30378* (2013.01); *A61F 2002/30484* (2013.01); *A61F 2002/30495* (2013.01); *A61F 2002/30497* (2013.01); *A61F 2002/30507* (2013.01); *A61F 2002/30607* (2013.01); *A61F 2002/4018* (2013.01); *A61F 2002/4022* (2013.01); *A61F 2002/4037* (2013.01); *A61F 2002/4051* (2013.01); *A61F 2002/4074* (2013.01); *A61F 2002/4085* (2013.01)

(58) Field of Classification Search
USPC .................... 623/18.11–19.14, 22.11–22.46
See application file for complete search history.

(56) References Cited

U.S. PATENT DOCUMENTS

| | | | | |
|---|---|---|---|---|
| 4,263,681 | A * | 4/1981 | Notton | 623/18.11 |
| 7,011,686 | B2 * | 3/2006 | Ball et al. | 623/19.14 |
| 2006/0142871 | A1* | 6/2006 | Biss et al. | 623/23.42 |
| 2008/0234830 | A1 | 9/2008 | Hershberger et al. | |
| 2009/0118837 | A1* | 5/2009 | Winslow et al. | 623/19.14 |
| 2010/0049327 | A1* | 2/2010 | Isch et al. | 623/19.12 |
| 2010/0161066 | A1* | 6/2010 | Iannotti et al. | 623/19.11 |
| 2011/0118846 | A1* | 5/2011 | Katrana et al. | 623/19.13 |

FOREIGN PATENT DOCUMENTS

| | | |
|---|---|---|
| DE | 10123517 C1 | 11/2002 |
| FR | 2852229 | 9/2004 |
| WO | WO-2008067400 A2 | 6/2008 |

OTHER PUBLICATIONS

International Search Report and Written Opinion of the International Searching Authority regarding International Application No. PCT/US2012/058255, mailed Dec. 12, 2012.

* cited by examiner

*Primary Examiner* — Yashita Sharma
(74) *Attorney, Agent, or Firm* — Harness, Dickey (57) ABSTRACT

A prosthesis to replace a portion of the anatomy, such as the humerus, can include a first shell. A second prosthesis can be positioned relative to the shell to provide the bearing surface to articulate with a glenoid prosthesis or glenoid. The second prosthesis can include a connection portion to engage a connection portion in the shell.

10 Claims, 8 Drawing Sheets

MULTIPLE BEARING HUMERAL PROSTHESIS

CROSS-REFERENCE TO RELATED APPLICATIONS

This application claims the benefit of U.S. Provisional Application No. 61/543,477, filed on Oct. 5, 2011. The entire disclosure of the above application is incorporated herein by reference.

FIELD

The present disclosure relates to a modular prosthesis, and particularly to a humeral prosthesis including a plurality of bearings operable to interconnect with a single shell in a humeral prosthesis.

BACKGROUND

The statements in this section merely provide background information related to the present disclosure and may not constitute prior art.

Figure 1:
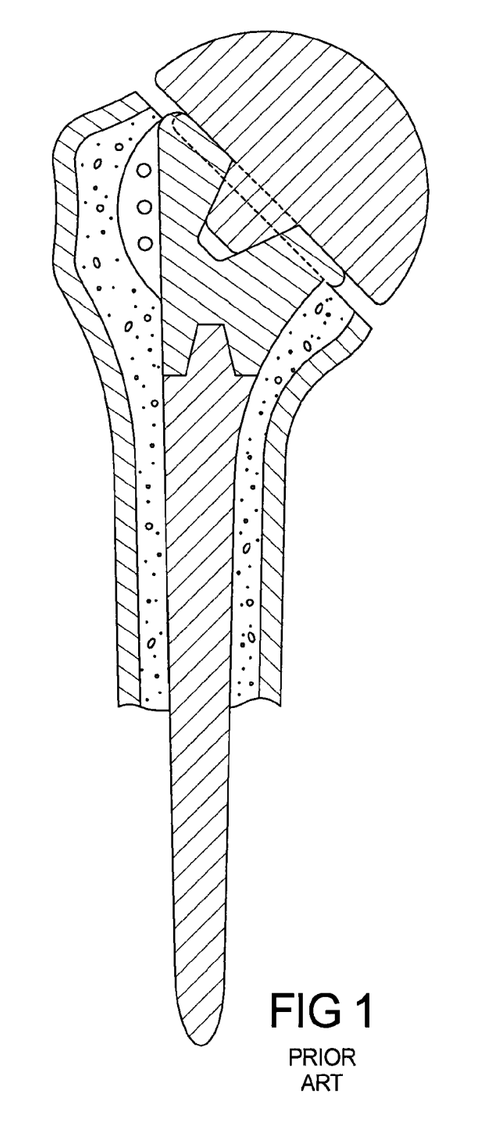
FIG. 1 represents a humeral prosthesis according to the prior art.

Articulating regions of the anatomy can include areas where two bone sections move relative to one another. For example, a humerus can provide a region for articulation with a glenoid bearing. The articulating region, however, can become injured or worn, and can therefore be replaced with various prostheses. Prostheses can replace the glenoid, the humeral head, various other portions of the humerus, or combinations thereof (see FIG. 1). The replacement of both the glenoid and the humeral head is generally referred to as a total joint replacement.

The total joint replacement of the glenoid and the humeral head requires a bearing or articulating surface for both the humeral head and the glenoid. The articulating surfaces are generally positioned relative to the various portions of the remaining natural anatomy in a substantially fixed manner. Materials must be selected for the bearing surfaces for various purposes, and are dependent upon patient defined parameters such as age, musculature, or expected activity level.

SUMMARY

This section provides a general summary of the disclosure, and is not a comprehensive disclosure of its full scope or all of its features.

A prosthesis to replace a portion of the anatomy, such as the humerus can include a first portion, such as a cup or shell, that can be fixed to, for example, a resected humerus. The humerus can be prepared in any appropriate manner to receive fixation of the cup. The prosthesis can include a second portion, such as a concave bearing or convex bearing, which can be positioned relative to the shell to provide a bearing surface to articulate with a glenoid prosthesis. It will be understood, however, that a selected bearing component can be provided to articulate or provide a bearing surface relative to a natural glenoid.

The prosthesis system can include a single shell that can be interconnected with two or more bearing members. The bearing members can include various characteristics or material selections, such as a polymer bearing and a metal bearing. The polymer bearing can provide a relatively soft surface for a member to bear against. The metal bearing, relative to the polymer bearing, can provide a substantially hard or tough surface to bear against. The different bearing materials can also include different connection portions to interconnect with the shell. The shell can include connecting regions to connect with the multiple bearing members, including both convex and concave bearing members.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings described herein are for illustrative purposes only of selected embodiments, and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. Although various embodiments are discussed below, including exemplary materials, it will be understood that any appropriate materials or combinations may be selected for use with the kits and/or assemblies of the present teachings. Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Figure 2:
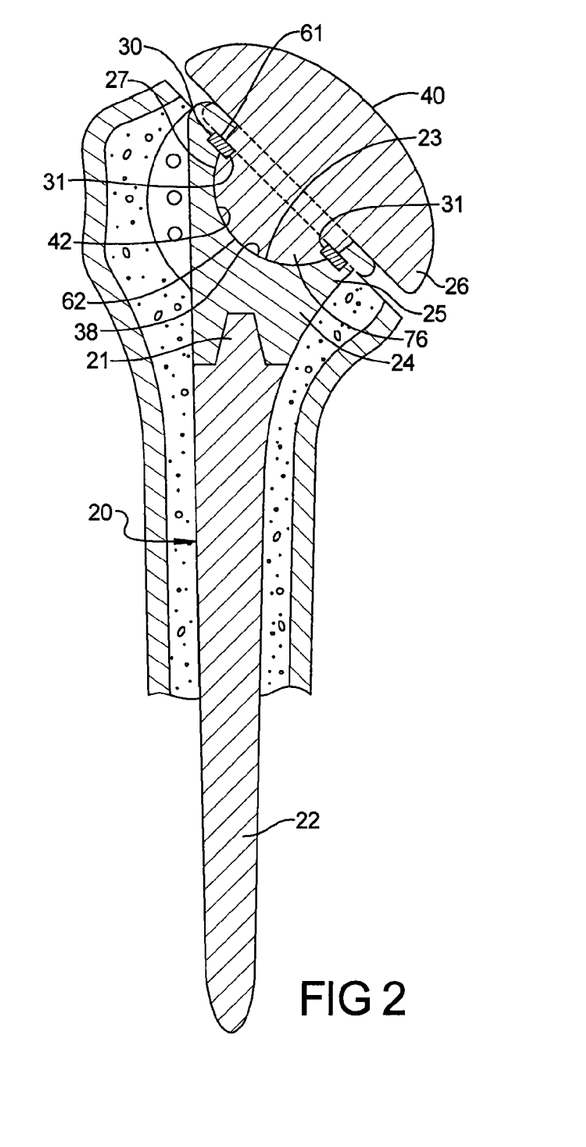
FIG. 2 represents a humeral prosthesis according to the present teachings.

FIG. 2 represents one example of a humeral prosthesis 20 according to the present teachings. As will be discussed in greater detail below, the humeral prosthesis embodiments disclosed herein can be included in a kit, such as a humeral implant kit, for use in a partial or total shoulder joint replacement. According to various embodiments, the kits can include various humeral components of differing sizes and configurations, such as humeral shells, bearings and coupling members, to accommodate partial and total shoulder joint replacements, including reverse shoulder prosthesis configurations.

Figure 3:
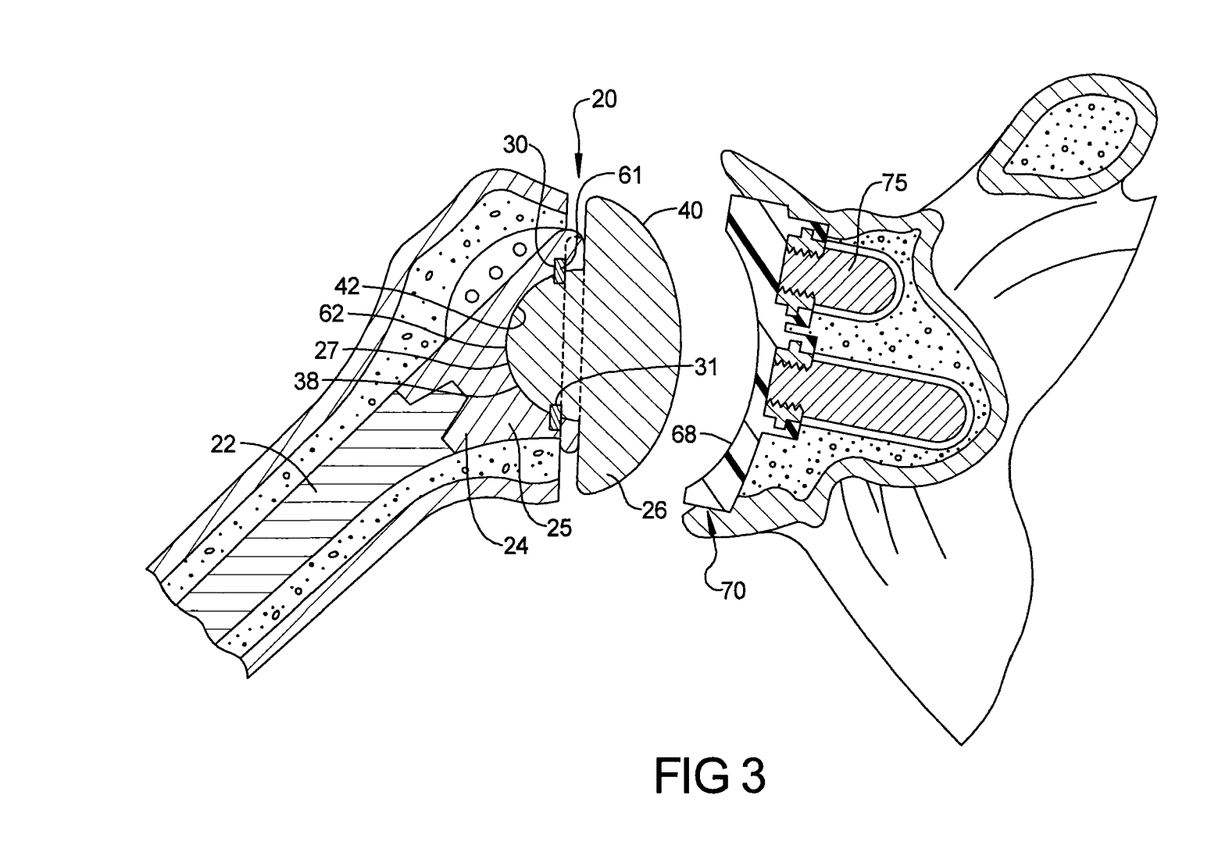
FIG. 3 represents a total shoulder prosthesis according to one embodiment of the present teachings.

With additional reference to FIG. 3, the humeral prosthesis 20 can include a stem 22 coupled to a head coupling member 24 and a first bearing member 26. In one embodiment, the head coupling member 24 can define a generally spherical or cylindrical coupling aperture 27 forming a void or passage 76. Defined within the head coupling member 24 can be a shell 25, which can define the coupling aperture 27. The coupling aperture 27 can include a defined interior coupling groove 30. An apical location 21 of the shell 25 can define a coupling mechanism used to couple the stem 22 to the head coupling member 24.

Figure 5:
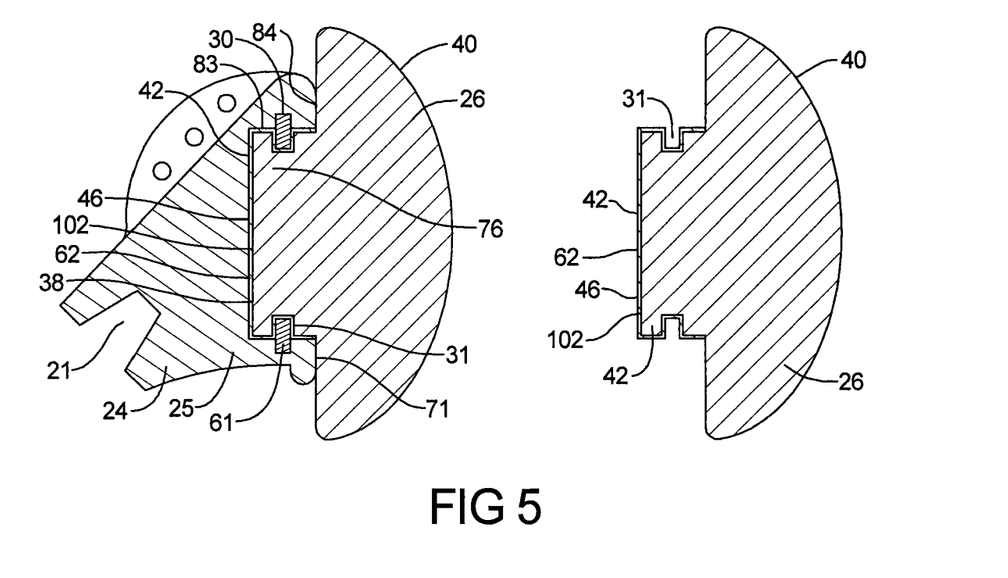
FIGS. 5 and 6 represent views of a humeral prosthesis according to an alternate embodiment of the present teachings.
Figure 6:
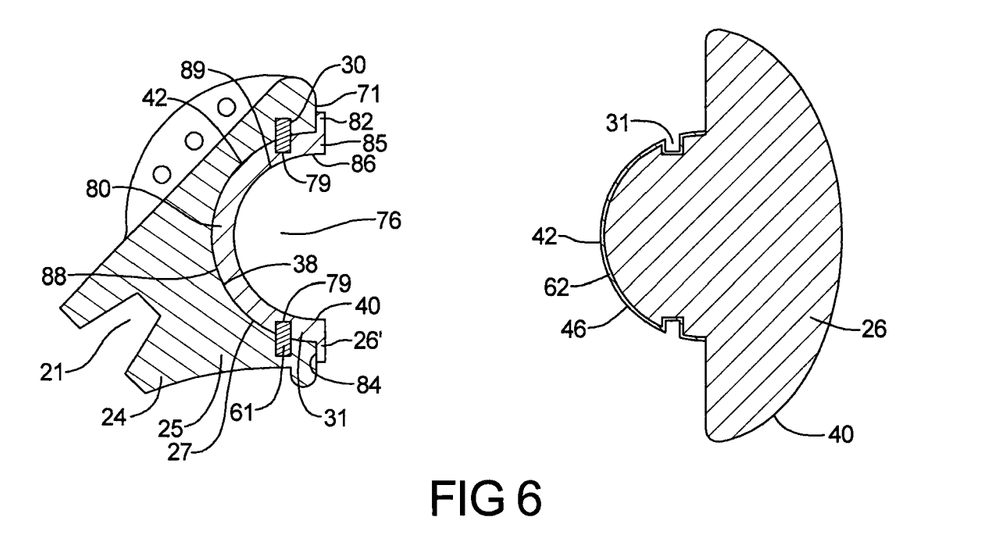

The interior coupling groove 30 can be configured to couple the first bearing member 26 to the head coupling member 24. As best seen in FIGS. 2, 5 and 6, the first bearing member 26 can have a convex or concave articulating bearing surface 40 and an opposite coupling side 42. The coupling side 42 can define an exterior coupling groove 31, which can interface with a coupling member or snap-ring 61 to fix the first bearing member 26 to the head coupling member 24 via a ringlock connection. Additionally, the coupling side 42 can have a convex surface configured to interface with the spherical or cylindrical coupling aperture 27. The coupling side 42 can have a polymer exterior surface, or can have a metallic exterior sleeve or layer 46, as will be discussed in greater detail herein. The first bearing member 26 can be formed of a substantially hard or rigid material, including ceramic, UHMWPE material, metal or metal alloys.

The ringlock connection, such as in the RingLoc® humeral implant sold by Biomet, Inc. of Warsaw, Ind., USA, can offer a substantially fixed position of the first bearing member 26 in both an axial position and rotational position relative to the shell 25. The ringlock can have tabs to facilitate coupling the snap-ring 61 into the coupling or ringlock grooves 30, 31.

As best seen in FIGS. 2-3, the first bearing member 26 includes the first articulating bearing surface 40, which can have a first radius of curvature. The opposite coupling side 42 of first bearing member 26 can have a convex curved coupling or exterior surface 62 having a second radius of curvature which is less than the first radius of curvature. The convex curved coupling surface 62 can be a sphere (e.g., FIGS. 2, 3 and 6) or an exterior surface of a cylinder (e.g., FIG. 5), as will be discussed below in greater detail. The exterior coupling groove 31 can be defined at a location between the articulating bearing surface 40 and the coupling side 42.

The coupling surface 62 of first bearing member 26 can be configured to cooperate with an interior surface 38 of coupling aperture 27 of shell 25. The interior surface 38 of the shell 25 can be provided in any appropriate manner, such as substantially highly polished or substantially smooth. The interior surface 38 can contact exterior surface 62 of the coupling side 42 of the first bearing member 26 substantially tightly or with any appropriate gaps. The interior surface 38 can contact the exterior surface 62 completely or in part, according to various embodiments.

As best seen in FIG. 3, the radius of curvature of the bearing surface 40 can conform to the radius of curvature of an articulating surface 68 of a glenoid prosthesis 70. The glenoid prosthesis 70 can have a traditional concave bearing surface for a shoulder replacement, or in a reverse shoulder arrangement 72 (discussed below in greater detail with reference to FIG. 4), can have a convex bearing surface. The glenoid prosthesis 70 can be coupled to a glenoid using fixed or removable pegs 75.

Figure 4:
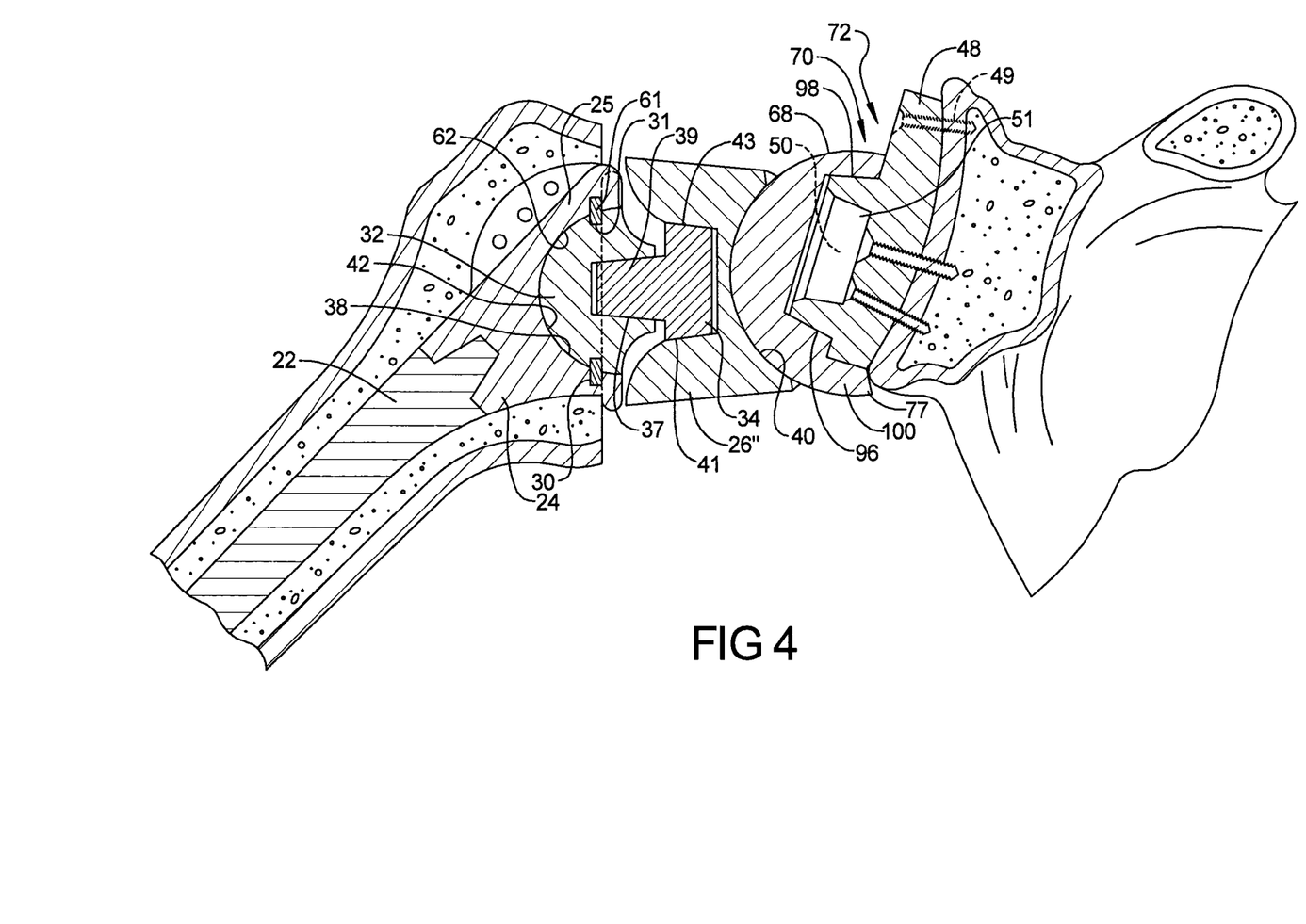
FIG. 4 represents a reverse shoulder prosthesis according to an alternate embodiment of the present teachings.

With reference to FIG. 4, the shell 25 can accommodate provisions for a reverse shoulder bearing configuration 72. In this regard, the shell 25 can be used to couple intermediate coupling members 32 and 34, which can be used to couple a second bearing 26" having a concave articulating bearing surface 40 defined thereon. Coupling member 32 can have a curved coupling surface 62 defined on the coupling side 42, which can interface with the interior surface 38 of the coupling aperture 27 of shell 25. Intermediate coupling member 32 can be coupled to the shell 25 using the snap-ring 61 in a similar manner as discussed above for first bearing member 26. Intermediate coupling member 32 can also have a locking taper 37 defined therein.

The locking taper 37 can be configured to engage a corresponding locking taper 39 that can be defined on coupling member 34. Additionally, a second locking taper 41 can be defined by a portion of coupling member 34, and can be configured to engage a locking taper 43 defined in the bearing 26".

The glenoid portion of the reverse shoulder bearing configuration 72 can include an intermediary member 48 coupled to the glenoid with a plurality of fasteners 49. Fasteners 49 can be the same as, or different from the fasteners 75 shown in FIG. 3. The intermediary member 48 can have provisions to accept various sized convex bearings 100, as shown in FIG. 4. These convex bearings 100 can have a male locking taper 50 configured to engage a female taper 51 defined in the intermediate member 48. In the exemplary configuration illustrated, the bearings 100 can define a female taper 96 configured to be coupled to a male taper 98 defined about the female taper 51. An articulating surface 68 of the bearing 100 can be configured to rotatably engage bearing surface 40 of second bearing 26".

Figures 8, 9:
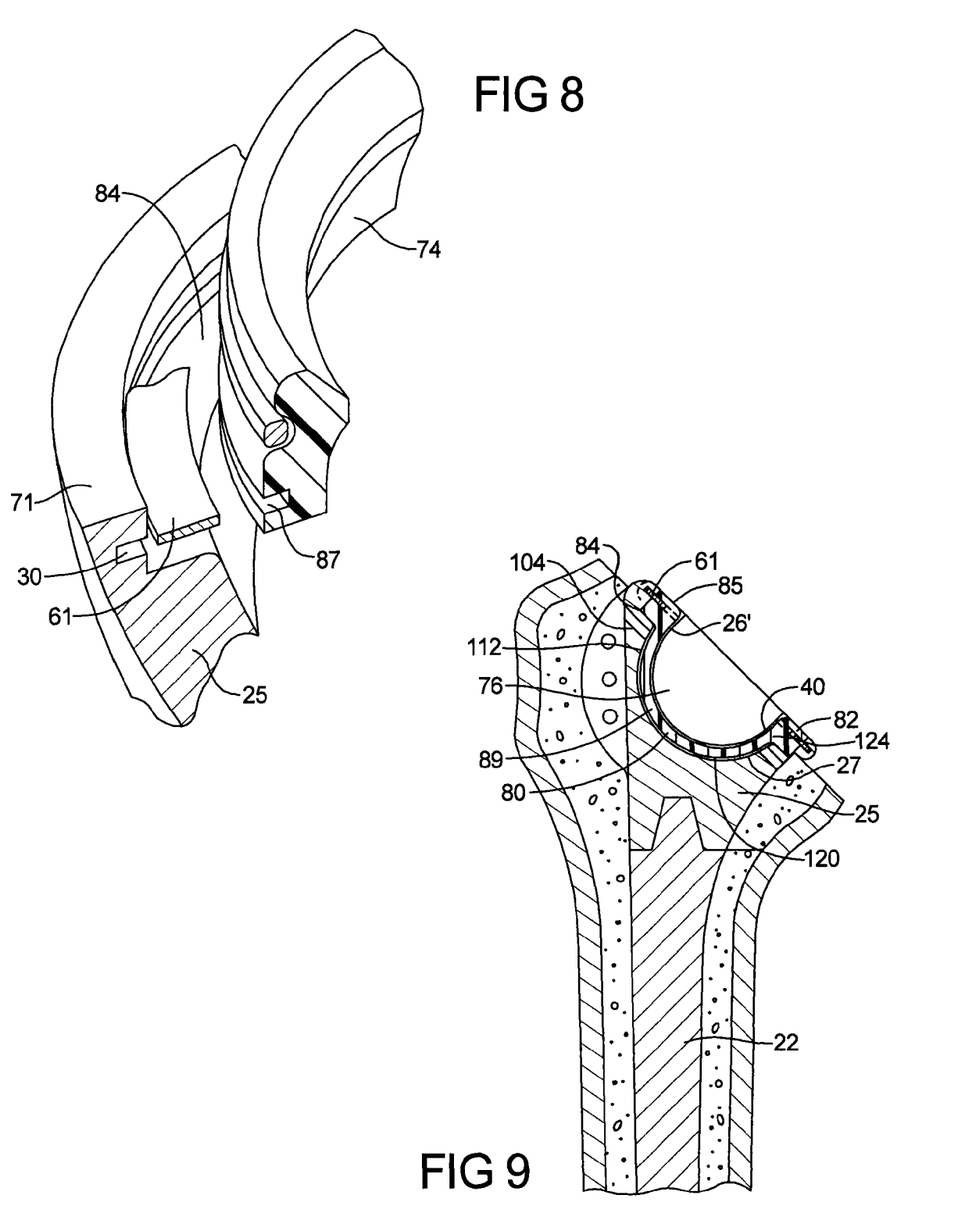
FIGS. 8 and 9 represent sectional views of various embodiments according to the present teachings.

With continuing reference to FIG. 4 and additional reference to FIGS. 6 and 9, the coupling aperture 27 can function to fix an alternative first bearing member 26', shown in the form of a concave bearing cup 80, to the head coupling member 24. The alternative first bearing member 26' can be formed of any appropriate materials, such as polymers including ultra-high molecular weight polyethylene (UHMWPE) or polyetheretherketone (PEEK). As will be discussed in greater detail below, the alternative first bearing member 26' can include a concave articulating bearing surface operable to articulate with a selected member, such as a natural glenoid or a prosthesis glenoid implant.

As shown in FIG. 6, the alternative first bearing member 26' or bearing cup 80 can include an outer lip 82 which can bear against an exterior bearing ledge 84. The bearing cup 80 can have an extended portion 85 in the form of a cylindrical member 86, which can lead to a concave articulating surface 89. Similar to first bearing member 26, the snap-ring 61 can fixedly hold the bearing cup 80 or alternative first bearing member 26' relative to the shell 25, at least in an axial position. In this regard, the bearing cup 80 can include an external groove 79 similar to exterior coupling groove 31 of first bearing member 26, as shown for example in FIG. 6. The exterior groove 79 can align with the interior groove 30 of shell 25 when the first bearing member 26' is positioned in coupling aperture 27, as also shown in FIG. 6. In particular, an external surface 88 of the first bearing member 26' can engage the interior surface 38 of the coupling aperture 27 of shell 25 and the snap-ring 61 can couple bearing 26' to shell 25 in a similar manner as first bearing member 26 discussed above.

The alternative first bearing member 26' can also include any appropriate size for positioning in the shell 25. The first bearing member 26' can be selected to include the concave articulation surface 89 for articulation relative to the reverse glenoid implant configuration 72 shown in FIG. 4. In this particular configuration, the first bearing member 26' can be configured to replace the intermediate coupling members 32 and 34 and the second bearing member 26" shown in FIG. 4, such that the concave articulation surface 89 of the alternative first bearing member 26' engages the articulation surface 68 of the convex bearing 100. In this regard, the curvature of the articulation surface 68 can be configured to mate with the curvature of the articulation surface 89 of the first bearing member 26'.

Optionally, as seen in FIG. 9, the alternative first bearing member 26' or bearing cup 80 can be incorporated fully within the shell 25. For example, a first exterior wall portion 120 of the alternative first bearing member 26' can engage a substantially hemispherical or semispherical inner wall 112 of the shell 25. The first bearing member 26' can also include an engagement flange 124 that is operable to engage an internal bearing region 104 of the shell 25. The internal bearing region 104 can provide a ringlock connection. Optionally, the snap-ring 61 can also be used to couple first bearing member 26' to shell 25, as shown in FIG. 9. In this exemplary configuration of shell 25 and first bearing member 26', grooves for receiving snap-ring 61 can be positioned relative to the outer lip 82 of bearing 26' and the engagement flange 124 of shell 25, as also shown in FIG. 9.

As best seen in FIG. 5, the shell 25 can optionally include a cylindrical coupling surface 83 configured to cooperate with a cylindrical coupling surface 102 of the first bearing member 26. Optionally, the snap-ring 61 can be coupled to the shell 25 and the cylindrical surface 102 in the same manner as discussed above for the spherical coupling configuration of first bearing member 26. As discussed above, the snap-ring 61 can be used to regulate rotation of the humerus with respect to the stem. As shown, the bearing 26 can have an articulating surface having a varying diameter or center of rotation.

As depicted throughout, the first bearing members 26, 26' can include a metal coated or sleeved polymer. The metal coating or layer 46 can be a stamped or machined component. The first bearing member 26 can be insert molded or pressed into the metal layer or member 46. The metal layer 46 can also define the coupling groove which facilitates the coupling of the bearing member 26 to the shell 25, as shown for example in FIGS. 5 and 6. In addition, the alternative first bearing member 26' can optionally include a metal coated or sleeved polymer layer, as shown for example in FIG. 9.

Briefly, the provision of the first bearing members 26, 26' allows for a pre-operative or intra-operative selection of bearings for positioning within the shell 25. In addition, or alternatively, the provision of the first bearing members 26' that can engage the shell 25 can minimize the number of parts for a procedure. Each of a plurality of the first bearings 26, 26' can also include different dimensions, such as an internal diameter, an external diameter, etc.

The shell 25 can also be provided in different sizes or configurations. For example, a diameter or height of the shell 25 can be altered based upon different portions that articulate with the first bearing members 26 and 26', the size of the patient, or other appropriate considerations. The shell 25 defined by a shell wall portion or member can also be provided in multiple thicknesses.

Figure 7:
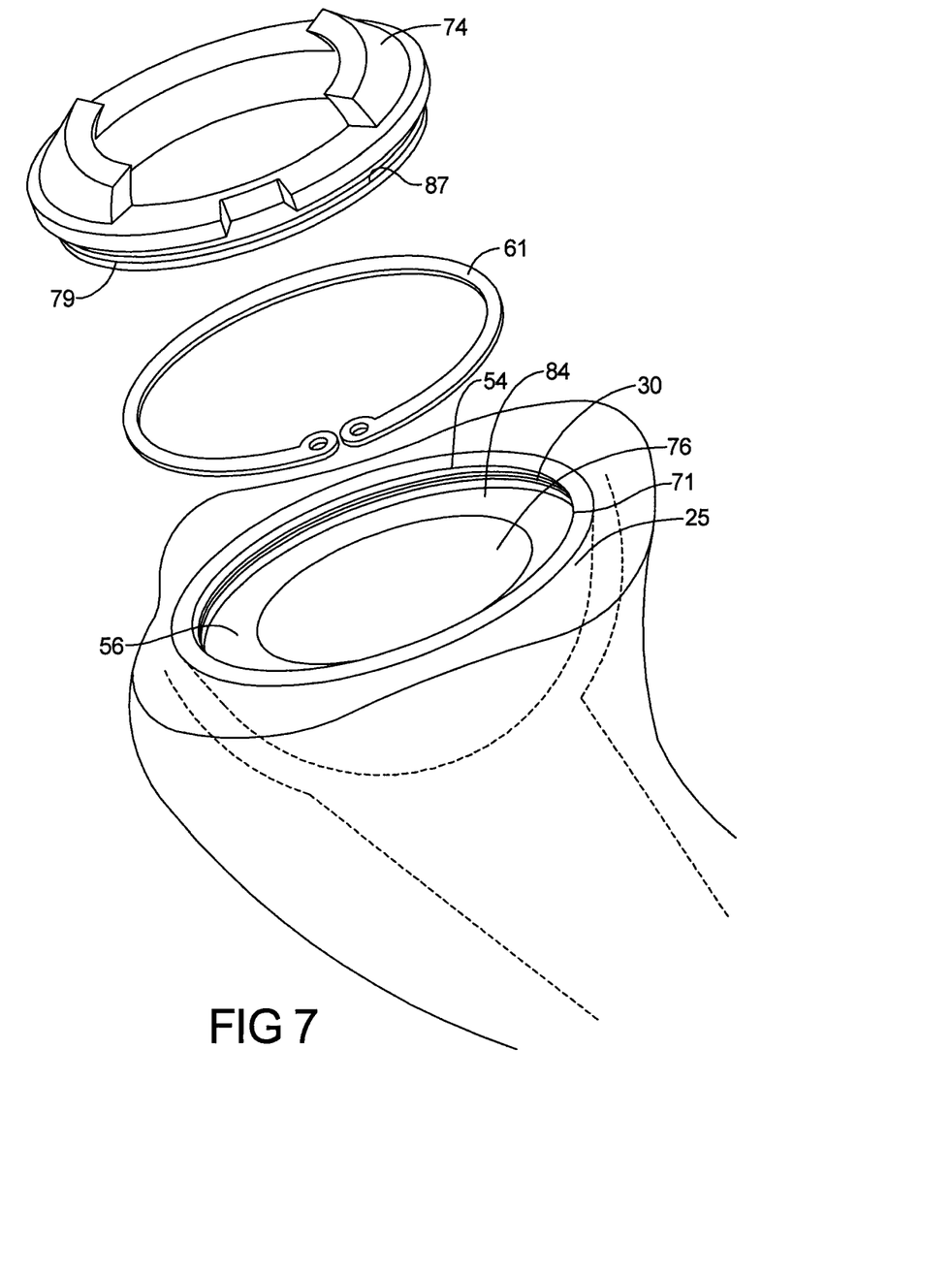
FIG. 7 represents an alternate humeral prosthesis according to the present teaching.

As can be seen in FIGS. 7 and 8, a humeral assembly, according to various embodiments, includes the shell 25 relative to which the first bearing member 26 can be positioned. As shown in FIG. 7, shell 25 can include a first thickness 54 that can be less than a second thickness 56. Defined between these thicknesses can be bearing ledge 84. The first and second thicknesses 54, 56 can also alter or change the dimensions of the snap-ring 61. In this regard, it will be understood, however, that a system or kit of the shells 25 and the first bearing members 26, 26' can include multiple sizes of the components included therein.

As also shown in FIGS. 7 and 8, a constraining ring 74 can be associated with the shell 25 and configured to cooperate with first bearing member 26 to retain bearing member 26 relative to shell 25. The constraining ring 74 can include a groove 87 configured to receive a portion of snap-ring 61 when positioned in shell 25 relative to bearing ledge 84 and rim 71. In this exemplary configuration, the snap-ring 61 can function to couple constraining ring 74 to shell 25 via the ringlock connection, which can thereby couple first bearing member 26 to shell 25.

Figure 13:
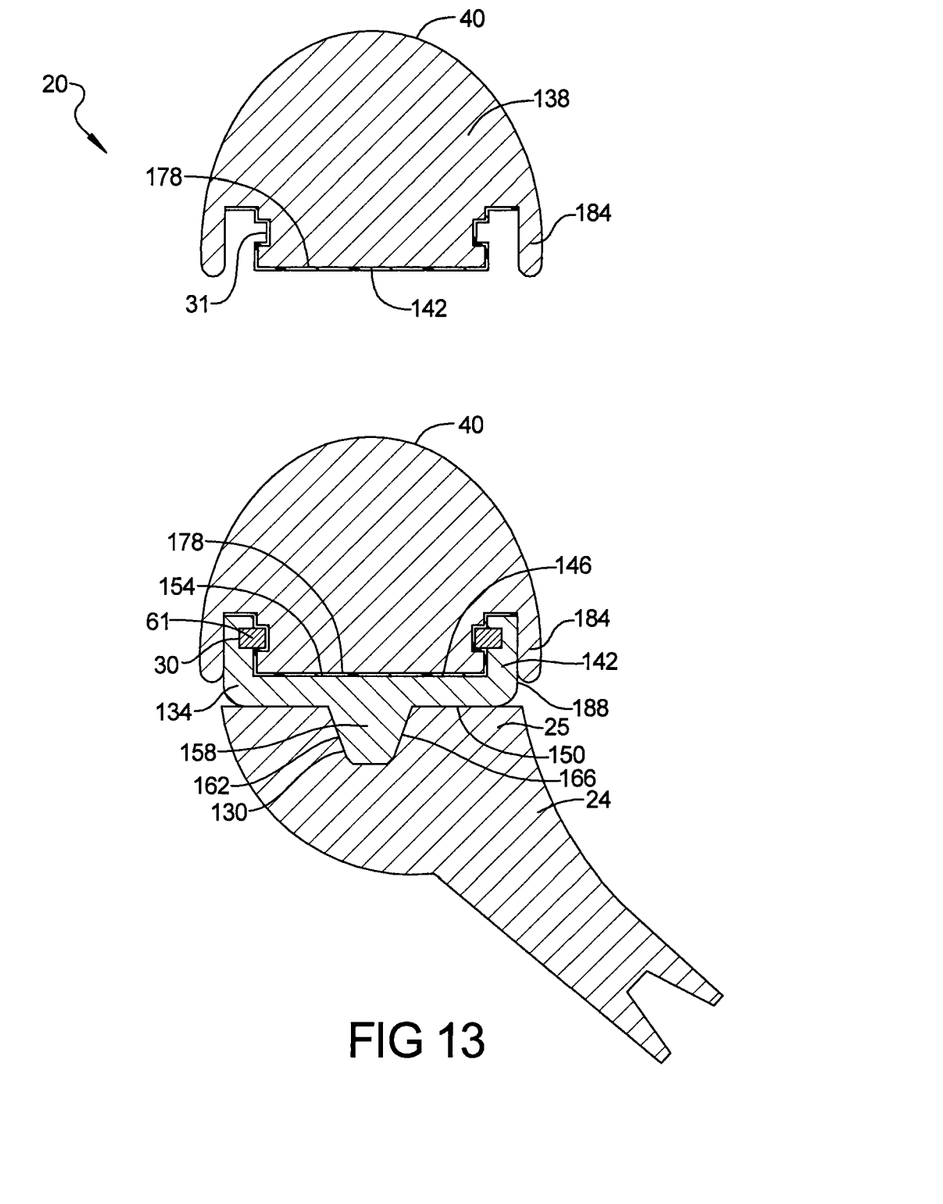
FIG. 13 represents an alternate humeral prosthesis according to the present teachings.

With additional reference to FIG. 13, an alternate humeral prosthesis 20 is shown in accordance with the present teachings. Humeral prosthesis 20 can include the shell 25 having a coupling arrangement 130 configured to receive a humeral tray 134. As will be discussed below in greater detail, the humeral tray 134 can be configured to receive the first bearing member 26, such as bearing 26 shown in FIG. 5, or an alternate first bearing member 138 shown in FIG. 13.

In one exemplary configuration, humeral tray 134 can include a body 142 defining a bearing coupling side 146 and an opposite shell coupling side 150. The body 142 can define a recess 154 for receiving the coupling side 42 of the first bearing member 26 or 138. The bearing coupling side 146 can also define an interior coupling groove 30 configured to receive the snap-ring 61, as shown in FIG. 13. The shell coupling side 150 can include a coupling member 158 in the form of a tapered male projection or locking taper 162 configured to be received in a corresponding tapered female recess or locking taper 166 defined by shell 25.

The first bearing member 138 and the humeral tray 134 can be formed of a suitable metallic material, such as cobalt chromium or titanium. In this exemplary configuration, the first bearing members 26 and 138 can include a polymeric sleeve 178 such that the sleeve 178 engages the tray and snap-ring 61 as shown in FIG. 13. The first bearing member 138 can also be formed to include an optional extension 184 extending from a perimeter of the bearing member 138, as also shown in FIG. 13. The extension 184 can extend along an outer perimeter 188 of the humeral tray 134 and can provide increased bearing coverage. It should be understood that first bearing member 138 can be formed and/or utilized with or without the sleeve 178 and extension 184.

Shown throughout the figures are prostheses and components for a humeral implant kit for positioning various prostheses in a shoulder joint. The kit can include a humeral component having a shell defining a bearing accepting aperture. As discussed above, the shell can include a shell wall that extends from a distal apex portion to a proximal rim defining an internal passage or aperture operable to receive bearing components. The shell wall can include an internal shell wall surface defining the internal aperture or void and an external shell wall surface operable to engage a resected head of the humerus. Defined in the interior surface is a snap-ring mechanism, which can include a groove formed in the apical wall at a position between the internal shell wall surface and the external shell wall surface configured to receive the snap-ring.

As discussed above, the kit can have coupling stems of various sizes which can be formed by the shell. Additionally, as shown in FIGS. 10-12, the coupling stems 22 can be coupled to the shell 25 using expandable mating tapers 125.

Figure 10:
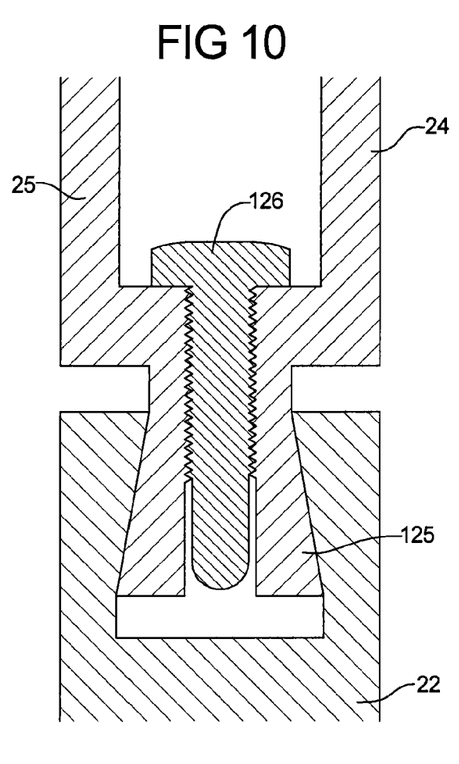
FIGS. 10-12 represent stem coupling mechanisms according to the present teachings.
Figure 11:
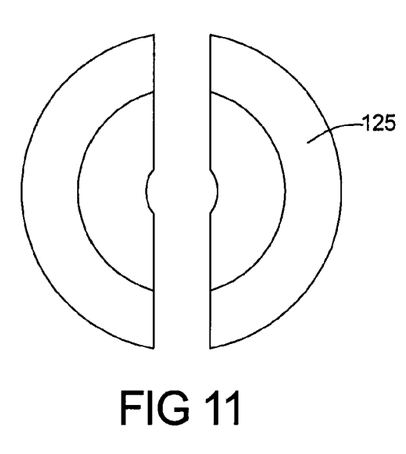
Figure 12:
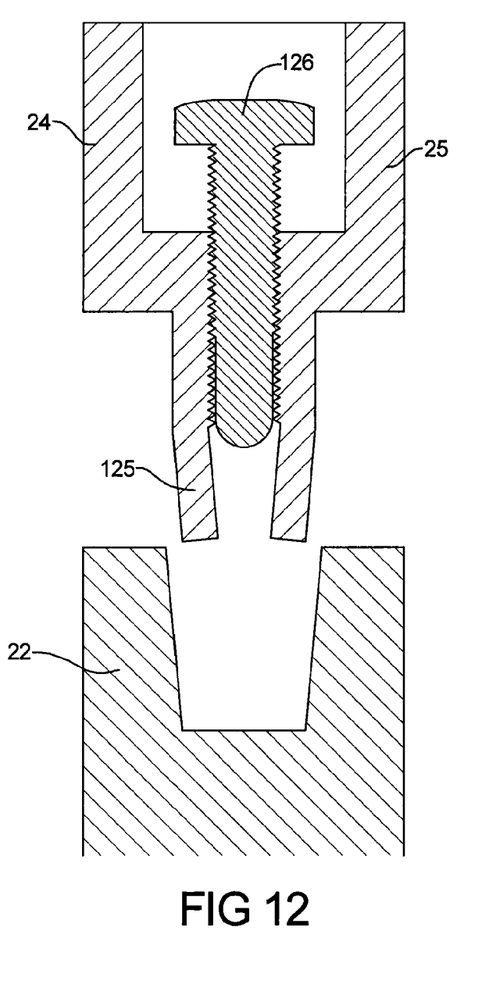

These tapers 125 can be split in a manner which allows expansion using an interference rotatable fastener 126, as shown in FIGS. 10-12.

The bearing components provided in the kit can include the first bearing member 26, and the alternative first bearing member 26'. As discussed above, the first bearing member 26 can define a concave articulating bearing surface and having a first bearing wall extending from a first bearing distal rim. The bearing wall can define a snap-ring connection mechanism configured to be aligned to the snap-ring mechanism associated with the shell. The first bearing member 26' can define a convex articulating bearing surface and a second bearing coupling mechanism extending from a second bearing distal apex. In one exemplary configuration, the first bearing member 26 can have a rigidity that is greater than a rigidity of the first bearing member 26', and the bearing members 26, 26' can be formed of different materials. A snap-ring connection mechanism can be formed adjacent the second bearing distal rim and between the convex coupling mechanism and the convex articulating bearing surface.

In practice, a humeral shell 25 which conforms to the resected humerus can be selected by a treating physician. The selected shell 25 can include the first stem 22 with a first connection portion at the apical location of the shell 25, and a second connection portion positioned at a second position relative to the shell 25. Upon a determination by the treating physician of an appropriate system, the physician can select one of the first bearing members 26, 26'. The humeral head can be resected and the selected shell 25 with the associated stem 22 can be inserted into the prepared humerus. The selected bearing can be axially inserted within the shell 25. The selected bearing can be connected with the second connection portion of the shell discussed above.

According to various embodiments, various bearings depicted throughout can engage other defined connection portions simultaneously or during or after implantation. Thus, one skilled in the art will understand that while discussion herein may be focused primarily upon connecting a bearing with the connection portion that a bearing can also be connected at various times of the procedure. The multiple connections can be provided for various reasons, such as securing the bearing at more than one location, guiding the bearing into an implantation position, reduction in manufacturing processes, etc.

These teachings are merely exemplary in nature, thus, variations that do not depart from the gist thereof are intended to be within the scope of the teachings. Such variations are not to be regarded as a departure from the spirit and scope of these teachings.

What is claimed is:

1. A humeral implant kit, comprising:
a shell having:
a shell wall that extends from a distal apex portion to a distal rim defining a passage operable to receive a bearing, wherein the shell wall has an internal shell wall surface defining an internal void and an external shell wall surface operable to engage the humerus;
a coupling stem coupled to the shell;
a snap-ring connection mechanism formed in the shell near the distal rim;
a first bearing defining a concave articulating bearing surface and having a first bearing wall extending from a first bearing distal rim, the bearing wall defining a second snap-ring connection mechanism;
a second bearing defining a convex articulating bearing surface and having a second bearing wall extending from a second bearing distal apex, a third snap-ring connection disposed between the convex articulating bearing surface and the second bearing wall,
wherein the first and second bearings are alternatively attachable to the shell.

2. The humeral implant kit of claim 1, further comprising a connecting member separate from the shell and the second bearing.

3. The humeral implant kit of claim 1, wherein the shell includes a ledge that projects into the internal void from the shell wall between the internal shell wall surface and the external shell wall surface.

4. The humeral implant kit of claim 3, wherein the second bearing includes a second bearing ledge extending from the second bearing wall.

5. The humeral implant kit of claim 1, wherein the stem comprises a stem coupling taper.

6. The humeral implant kit of claim 1, wherein the snap-ring connection mechanism comprises a plurality of ring bearing surfaces.

7. The humeral implant kit of claim 1, wherein the first bearing has a first rigidity and the second bearing has a second rigidity greater than the first rigidity.

8. The humeral implant kit of claim 3, wherein the second bearing comprises a metal coating layer that defines the second coupling groove.

9. The humeral implant kit of claim 1, wherein the snap-ring connection mechanism of the shell includes a groove formed in the shell wall at a position between the internal shell wall surface and the external shell wall surface.

10. The humeral implant kit of claim 1, wherein the first and second bearing walls are interchangeably received by the shell wall.

* * * * *